United States Patent [19]

Ishida

[11] Patent Number: 4,974,811
[45] Date of Patent: Dec. 4, 1990

[54] ROLLER CLAMP FOR REGULATING FLUID FLOW THROUGH PLASTIC TUBE

[75] Inventor: Yoshihiro Ishida, Odate, Japan

[73] Assignee: Nissho Corporation, Osaka, Japan

[21] Appl. No.: 527,910

[22] Filed: May 24, 1990

[30] Foreign Application Priority Data

Jun. 14, 1989 [JP] Japan ................................ 1-151395

[51] Int. Cl.$^5$ ........................ F16K 7/06; F16L 55/14
[52] U.S. Cl. ......................................... 251/6; 604/34; 604/250
[58] Field of Search ................. 251/4, 6; 604/34, 250, 604/256

[56] References Cited

U.S. PATENT DOCUMENTS

| | | | |
|---|---|---|---|
| Re. 31,584 | 5/1984 | Adelberg | 251/6 |
| 3,533,439 | 10/1970 | Hall | 251/6 |
| 3,685,787 | 8/1972 | Adelberg | 251/6 |
| 3,960,149 | 6/1976 | Bujan | 251/6 |
| 4,013,263 | 3/1977 | Adelberg | 251/6 |
| 4,047,694 | 9/1977 | Adelberg | 251/6 |
| 4,238,108 | 12/1980 | Muetterties | 251/6 |
| 4,335,866 | 6/1982 | Bujan | 251/6 |
| 4,340,201 | 7/1982 | Becker, Jr. | 251/6 |
| 4,725,037 | 2/1988 | Adelberg | 251/6 |

FOREIGN PATENT DOCUMENTS

48-36526 5/1973 Japan.
60-27870 1/1985 Japan.

*Primary Examiner*—George L. Walton
*Attorney, Agent, or Firm*—Armstrong, Nikaido, Marmelstein, Kubovcik & Murray

[57] ABSTRACT

A roller clamp for regulating fluid flow through a plastic tube comprising a bottom plate for receiving the plastic tube, a pair of sidewalls each having a guide groove, and a roller wheel for pressing the plastic tube is disclosed. The bottom plate has a V-shaped channel along its longitudinal direction and a pair of projections each having a pointed end are formed on the top of lines each extending from the lowest position of the V-shaped channel. A required amount of fluid can be supplied at a constant flow velocity thanks to small tube resistance.

4 Claims, 4 Drawing Sheets

4,974,811

ROLLER CLAMP FOR REGULATING FLUID FLOW THROUGH PLASTIC TUBE

BACKGROUND OF THE INVENTION

The present invention relates to a roller clamp for regulating fluid flow through a plastic tube (hereafter referred to as roller clamp), and more particularly to a roller clamp capable of supplying a constant amount of fluid through a plastic tube by pressing a plastic tube with a roller wheel against a bottom plate having a pair of projections formed on the top of lines each extending from the lowest position of a V-shaped channel.

In a instillation assembly for supplying continuously to a patient liquid drug such as Ringer solution and liquid amino acid, or blood, a roller clamp provided in the midway of a fluid-guiding tube is widely used since the roller clamp can regulate an amount of fluid supplied to a patient.

As an example of such roller clamps, Japanese Examined Patent Publication No. 36526/1971 discloses a device for regulating fluid flow through a tube by pressing with a movable roller wheel a plastic tube inserted into a long and narrow, hollow box to deform the tube, i.e. to change a section of the tube. Further, as an improved device of the device disclosed in Japanese Examined Patent Publication No. 36526/1971, there is disclosed, in Japanese Examined Patent Publication No. 27870/1985 which corresponds to U.S. Pat. No. 4,013,263, a roller clamp wherein a bottom plate of a long and narrow box has a crosswise section shown in FIG. 4.

In FIG. 4, a plurality of raised portions 13, which are separated from each other by a plurality of discrete valley portions 15, are formed in the left side portion and right side portion of a V-shaped channel 14. A roller wheel 21 presses a plastic tube 22 to deform the tube 22, so that both ends of the tube 22 are surely fixed by a plurality of concaved or convexed portions on the side portion of the V-shaped channel 14. Fluid passes through a deformed inner space 16 formed in the central portion of the V-shaped channel 14.

However, when dripping infusion is carried out with arranging the above-mentioned roller clamp in an instillation assembly, it has been found that the dripping number is reduced as time goes on, so that a required amount of fluid is not always supplied to a patient at a required flow velocity.

As a result of various investigation, the present inventor has found out that a supply speed of fluid can be stabilized by forming a pair of projections near a V-shaped channel as much as possible, and completed the present invention.

SUMMARY OF THE INVENTION

In accordance with the present invention, there is provided a roller clamp for regulating fluid flow through a plastic tube comprising a longitudinally extending bottom plate for receiving the plastic tube, a pair of sidewalls extending from both sides of the bottom plate and each having a guide groove, and a roller wheel having a shaft both ends of which are positioned in the groove and pressing the plastic tube placed on the surface of the bottom plate, the shaft slidably moving in the groove; the improvement wherein the surface of the bottom plate is inclined with respect to the guide groove, the bottom plate has a V-shaped channel along its longitudinal direction and a pair of projections formed on the top of lines each extending from the lowest position of the V-shaped channel, and the thickness of the bottom plate gradually reduces from the projection toward the sidewall.

The present invention further provides a roller clamp wherein a pair of guide grooves are formed to be approximately horizontal, the thickness of the bottom plate continuously and gradually increase in the longitudinal direction thereof, and the crosswise sectional area of the bottom plate continuously changes according to inclination of the surface of the bottom plate.

The present invention still further provides a roller clamp wherein the guide groove is inclined with respect to the bottom plate, and the crosswise sectional area of the bottom plate is substantially constant along its longitudinal direction.

The present invention further provides a roller clamp wherein a distance between a pair of projections is 35 to 70% with respect to the crosswise length of the bottom plate.

In a roller clamp of the present invention, a plastic tube is pressed by a roller wheel by sliding a shaft of the roller wheel along a guide groove and is fixed by a pair of projections formed on extending lines of a V-shaped channel. Fluid can be supplied at a constant flow velocity through a deformed inner space of the plastic tube with surely maintaining the plastic tube in a deformed condition.

DETAILED DESCRIPTION

Next, a roller clamp of the present invention is explained in detail based on the accompanying drawings.

Figure 1:
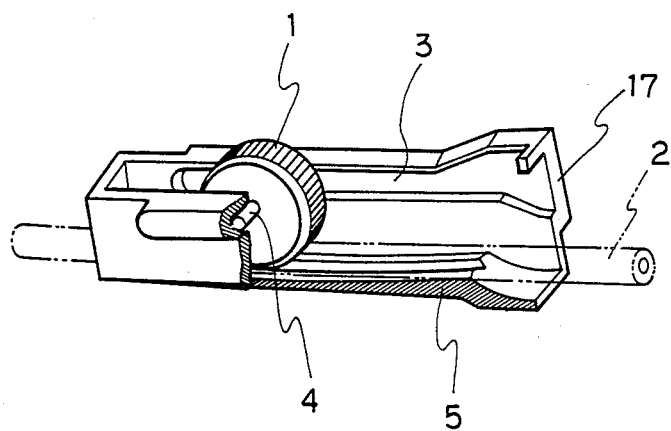
FIG. 1 is a perspective view of an embodiment of a roller clamp of the present invention.

In FIG. 1, numeral 3 is a pair of guide grooves formed approximately horizontally in sidewalls 17 which extend from both sides of a bottom plate 5. Both ends of a shaft 4 of the roller wheel 1 are positioned in the guide grooves 3 and designed to slidably move in the guide grooves 3. The surface of the bottom plate 5 is inclined with respect to the guide grooves 3. The thickness of the bottom plate 5 increases continuously and gradually in a longitudinal direction of the bottom plate 5. A plastic tube 2 is inserted between the roller wheel 1 and the bottom plate 5. A degree of pressing of the plastic tube 2 by the roller wheel 1 is adjusted with the movement of the roller wheel 1. That is, the sectional area of an inner space 7 of the plastic tube 2 is determined by the position of the roller wheel 1 in a longitudinal direction.

Figure 2:
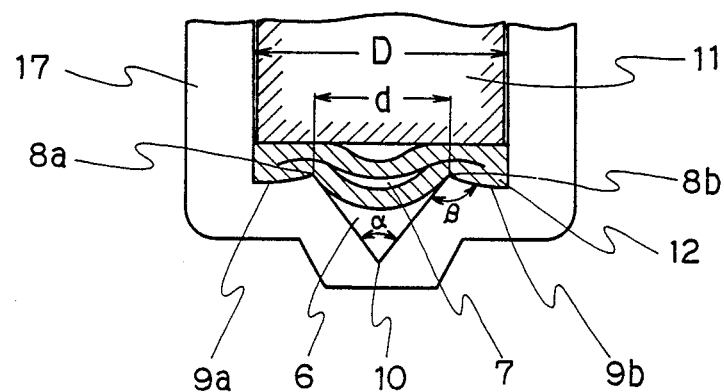
FIG. 2 is a crosswise sectional view of a roller clamp of the present invention.

FIG. 2 is a crosswise sectional view of a bottom plate 5 of roller clamp of the present invention. In FIG. 2, a pair of projections 8a, 8b are formed on the top of lines each extending from the lowest position 10 of a V-shaped channel 6 to side portions 9a, 9b. The thickness of the side portions 9a, 9b is reduced gradually from the projections 8a, 8b toward the sidewall 17. A plastic tube 12 inserted between the roller wheel 11 and the bottom plate 5 is pressed by the roller wheel 11, and is fixed at the projections 8a, 8b. Both ends of the plastic tube 12 are deformed to be flat so that an inner space 7 of the plastic tube 12 is almost disappeared. Thus, fluid cannot pass through both ends of the plastic tube 12 while only a small amount of fluid is supplied through the inner space 7 formed between projections 8a, 8b. Flow velocity of fluid passing through a plastic tube 12 is determined depending on the sectional area of the inner space 7.

The sectional shape of the lowest position 10 of the V-shaped channel 6 is not limited to a pointed one as shown in FIG. 2. It might be arc-shaped so long as an angle $\alpha$ between two lines extending from projections 8a, 8b toward the lowest position 10 is from 30 to 120 degrees, preferably from 50 to 90 degrees.

It is preferable that an angle $\beta$ at the projection 8b is approximately equal to that at the projection 8a. The angle $\beta$ is preferably 60 to 120 degrees, more preferably 70 to 100 degrees. When an angle at a projection is less than 60 degrees, a tip of the projection is liable to stick deeply into the plastic tube 12 and sometimes reach the inner space 7 thereof. On the other hand, when an angle at a projection is more than 120 degrees, the plastic tube 12 is not sufficiently fixed at projections when being pressed by the roller wheel 11 so that flow rate of fluid is liable to change.

Figure 3:
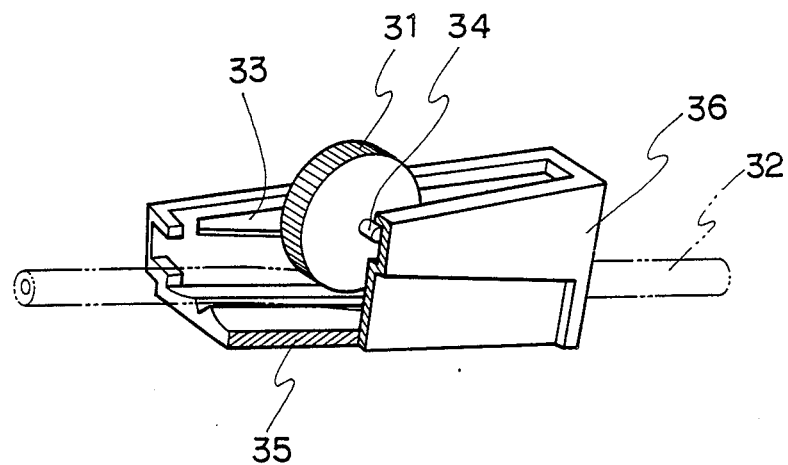
FIG. 3 is a perspective view of another embodiment of a roller clamp of the present invention.

FIG. 3 is a perspective view of another embodiment of a roller clamp of the present invention. In the embodiment of FIG. 3, an inclined guide groove 33 is formed on each of a pair of sidewalls 36 vertically extending from both sides of a long and narrow bottom plate 35. The bottom plate 35 has approximately equal thickness along its longitudinal direction. A shaft 34 of a roller wheel 31 is supported in the guide groove 33. A plastic tube 32 inserted between the bottom plate 35 and the roller wheel 31 is pressed by the slidable movement of the roller wheel 31 along the guide groove 33, so that flow rate of fluid passing through the plastic tube 32 is regulated.

The thickness of the bottom plate 35 of a roller clamp shown in FIG. 3 is approximately equal along its longitudinal direction. Distance d between a projection 8a and a projection 8b shown in FIG. 2 is preferably 35 to 70% to the width D of the bottom plate 35. When the ratio is less than 35%, the closing of an inner space 7 is liable to become loose since the plastic tube 12 is not sufficiently pressed by the roller wheel 11 at side positions 9a, 9b. On the other hand, when the ratio is more than 70%, regulation of flow rate of a small amount of fluid is liable to become difficult. As a material for a plastic tube, a flexible synthetic resin such as polyethylene, polypropylene and polyvinylchloride can be used.

Further, as a material of a roller clamp of the present invention, metal, synthetic resin, wood and the like can be used. Among them, synthetic resin such as polyethylene, polypropylene, polymethacrylate, polycarbonate, polyvinylchloride and ABS resin can be preferably used.

EXAMPLE 1

Figure 5:
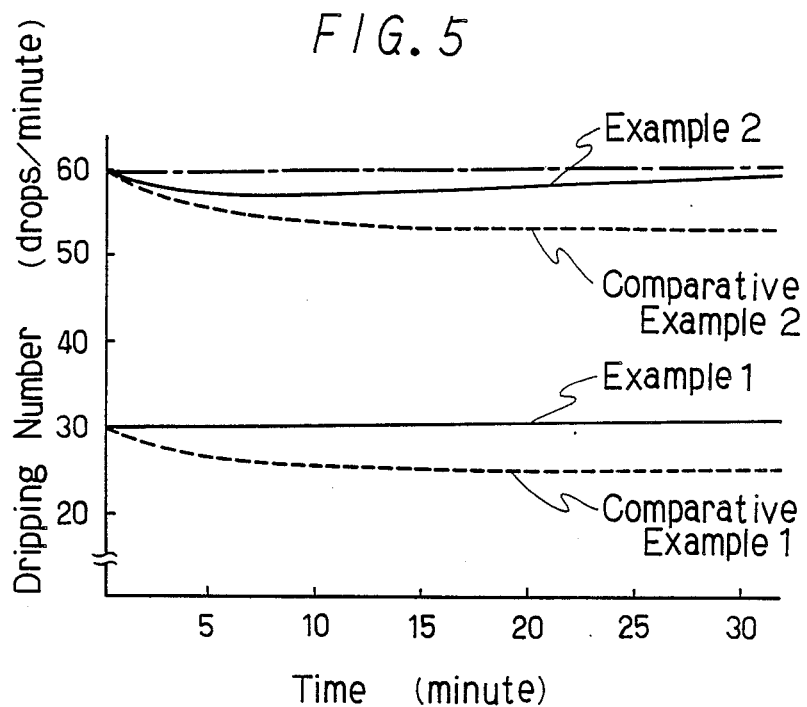
FIG. 5 is a graph showing change with time of the dripping number in a liquid infusion device.
Figure 6:
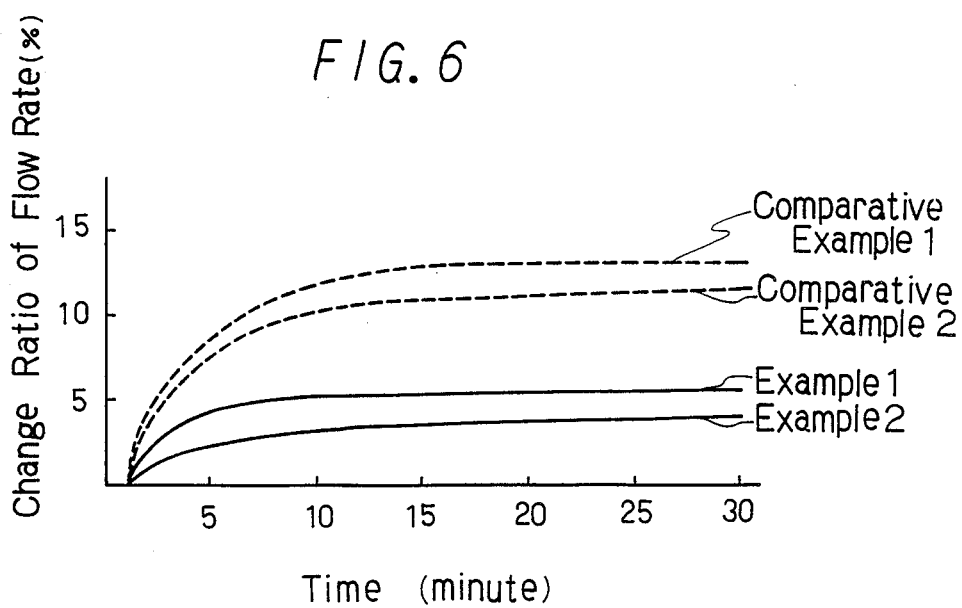
FIG. 6 is a graph showing change with time of change ratio in flow rate in the liquid infusion device.

A roller clamp made of polypropylene having such structure as shown in FIG. 1, wherein a shaft 4 of a roller wheel 1 made of ABS resin is engaged in a guide groove 3 of the roller clamp, was used. Diameter of the roller wheel 1 was 15.0 mm. A tube made of polyvinylchloride produced by Riken Chemical Co., Ltd. under the commercial name of TN-9281M having an outer diameter of 3.80 mm, an inner diameter of 2.64 mm and a thickness of 0.58 mm was inserted into the roller clamp. The roller wheel 1 was moved in such a manner that dripping speed became 30 drops per minute. The dripping test was carried out for 30 minutes using a test assembly shown in FIG. 7. The result of test is shown in FIG. 5. FIG. 6 is a graph showing change ratio of flow rate.

In the roller clamp used, an angle $\alpha$ and an angle $\beta$ of FIG. 2 were respectively 76 degrees and 105 degrees.

Figure 7:
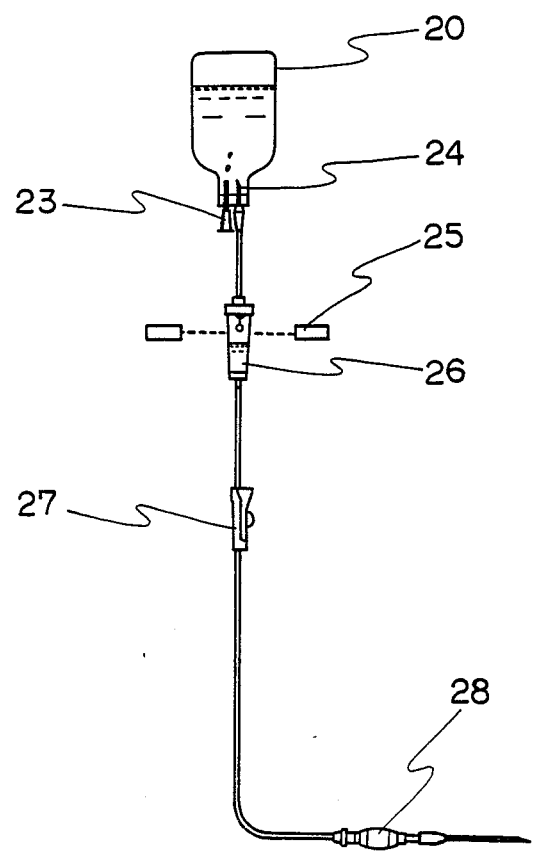
FIG. 7 is an explanatory view of a liquid infusion device used in the measurement in FIGS. 5 and 6.

FIG. 7 shows an instillation assembly used for testing performance of a roller clamp. In use, water is charged in a glass bottle 20 and then an injection needle 24 is sticked straight into a rubber plug. A roller wheel of a roller clamp 27 is positioned beforehand about 500 mm under the surface of water in the glass bottle 20. A tube is perfectly closed with the roller wheel. Next, the glass bottle 20 is turned upside down and hanged by a suitable hanger means (not shown). A dripping container 26 is crushed with fingers to fill about the half of the dripping container 26 with water. Water is flown out from an intravenous needle 28 by moving the roller wheel of the roller clamp 27 to perfectly discharge air in the tube. After discharge of air, the roller wheel is moved to close the tube again. Thereafter, a vent needle 23 is sticked into the rubber plug and the intravenous needle 28 is fixed about 1000 mm under the surface of water in the glass bottle 20. The roller wheel is loosened little by little to regulate dripping number to a required dripping number. A photoelectric tube 25 produced by Keyence Co., Ltd. under the commercial name of LX-130R is arranged to detect dripping from the dripping tube 26. The dripping number was recorded for 30 minutes with operating a dripping number counter produced by Citizen Watch Co., Ltd. under the commercial name of CBM-1320.

EXAMPLE 2

The same procedure as in Example 1 was repeated except that dripping number was changed from 30 drops per minute to 60 drops per minute. The result is shown in FIG. 5. FIG. 6 is a graph showing change ratio of flow rate.

COMPARATIVE EXAMPLE 1

Figure 4:
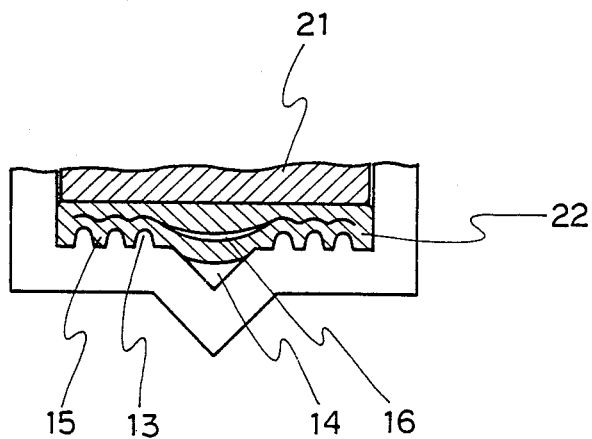
FIG. 4 is a crosswise sectional view of a conventional roller clamp.

The same procedure as in Example 1 was repeated except that a roller clamp having a crosswise section as shown in FIG. 4 was used instead of the roller clamp in Example 1. In the roller clamp of FIG. 4, height of a projection 13 was 0.2 mm and an angle formed by two inclined planes of a V-shaped channel was 90 degrees. Dripping test was carried out for 30 minutes after moving a roller wheel 21 in order to regulate dripping number to be 30 drops per minute. The result is shown in FIG. 5. FIG. 6 is a graph showing change ratio of flow rate.

COMPARATIVE EXAMPLE 2

The same procedure as in Comparative Example 1 was repeated except that dripping number was changed from 30 drops per minute to 60 drops per minute. The result is shown in FIG. 5. FIG. 6 is a graph showing change ratio of flow rate.

As is clear from FIGS. 5 and 6, change of dripping number and change ratio of flow rate of roller clamps in Example 1 and Example 2 are remarkably small in comparison with roller clamps in Comparative Examples. In FIG. 5, a chain line shows a set point of dripping number (60 drops per minute).

It is considered that scatter of dripping number is very small in the case of a roller clamp of the present invention since projections of the roller clamp are formed very near the V-shaped channel whereby reducing a tube resistance (i.e. reducing such a force that the tube is going to return its original shape), while scatter of dripping number is large in the case of a roller clamp of Comparative Example since projections are formed away from the V-shaped channel whereby increasing a tube resistance.

By using a roller clamp of the present invention in an assembly for continuously injecting blood, liquid drug and the like to a patient, a required amount of fluid such as blood and liquid drug can be supplied at a constant injection speed, whereby remarkably reducing danger to a patient.

What is claimed is:

1. In a roller clamp for regulating fluid flow through a plastic tube comprising a longitudinally extending bottom plate for receiving the plastic tube, a pair of sidewalls extending from both sides of the bottom plate and each having a guide groove, and a roller wheel having a shaft both ends of which is positioned in the groove and pressing the plastic tube placed on the surface of the bottom plate, the shaft slidably moving in the groove; the improvement wherein the surface of the bottom plate is inclined with respect to the guide groove, the bottom plate has a V-shaped channel along its longitudinal direction and a pair of projections formed on the upper end of lines each extending from the lowest position of the V-shaped channel and extending upwardly and forming the walls of the V-shaped channel, the thickness of the bottom sloping gradually downwardly and extending upwardly and forming the walls of the V-shaped channel from the projections toward the sidewall for pressing outer peripheral edges of said tube outwardly of said projections against said side walls as said roller wheel presses said tube against said projections and said bottom plate for effectively regulating fluid flow through said tube.

2. The roller clamp of claim 1, wherein the thickness of the bottom plate continuously and gradually increases in the longitudinal direction thereof, and the crosswise sectional area of the bottom plate continuously changes according to inclination of the surface of the bottom plate.

3. The roller clamp of claim 1, wherein the guide groove is inclined with respect to the bottom plate, and the crosswise sectional area of the bottom plate is substantially constant along its longitudinal direction.

4. The roller clamp of claim 3, wherein a distance between a pair of projections is 35 to 70% with respect to the crosswise length of the bottom plate.

* * * * *